(12) United States Patent
Campbell

(10) Patent No.: US 10,314,581 B2
(45) Date of Patent: Jun. 11, 2019

(54) RELOADABLE AND DISPOSABLE MULTIFUNCTIONAL SURGICAL DEVICE

(71) Applicants: Jean-Marc Galiana, Collonges au Mont d'Or (FR); Youssef Ismail, Caluire et Cuire (FR); Phillip Campbell, Shenzen (CN)

(72) Inventor: Phillip Campbell, Shenzen (CN)

(73) Assignees: Jean-Marc Galiana, Collonges au Mont d'Or (FR); Youssef Ismail, Caluire et Cuire (FR); Phillip Cambell, Shenzen (CN)

(*) Notice: Subject to any disclaimer, the term of this patent is extended or adjusted under 35 U.S.C. 154(b) by 418 days.

(21) Appl. No.: 15/037,384

(22) PCT Filed: Nov. 17, 2014

(86) PCT No.: PCT/FR2014/052926
§ 371 (c)(1),
(2) Date: May 18, 2016

(87) PCT Pub. No.: WO2015/071614
PCT Pub. Date: May 21, 2015

(65) Prior Publication Data
US 2016/0296232 A1 Oct. 13, 2016

(30) Foreign Application Priority Data
Nov. 18, 2013 (FR) ...................................... 13 61249

(51) Int. Cl.
*A61B 17/00* (2006.01)
*A61B 17/28* (2006.01)
(Continued)

(52) U.S. Cl.
CPC .... *A61B 17/07207* (2013.01); *A61B 17/1285* (2013.01); *A61B 2017/0023* (2013.01);
(Continued)

(58) Field of Classification Search
CPC ............ A61B 17/07207; A61B 17/068; A61B 17/105; A61B 17/1285;
(Continued)

(56) References Cited

U.S. PATENT DOCUMENTS 4,508,253 A * 4/1985 Green .................. A61B 17/072
227/120
5,336,229 A * 8/1994 Noda ............... A61B 17/12013
606/139
(Continued)

FOREIGN PATENT DOCUMENTS

EP 2537471 A1 12/2012

*Primary Examiner* — Robert F Long
(74) *Attorney, Agent, or Firm* — Jordan IP Law, LLC; Todd A. Vaughn

(57) ABSTRACT

A surgical device to perform open, endoscopic and/or laparoscopic surgical operations. The surgical device includes a handle assembly and at least one disposable loading unit. The handle assembly includes a casing forming a housing, a stationary handle element, and a handle element movable by way of an actuating movement. The at least one disposable loading unit may be reversibly mounted at least partially inside the casing, and includes an actuation mechanism.

15 Claims, 4 Drawing Sheets

(51) Int. Cl.
*A61B 17/29* (2006.01)
*A61B 17/072* (2006.01)
*A61B 17/128* (2006.01)

(52) U.S. Cl.
CPC ............... *A61B 2017/0046* (2013.01); *A61B 2017/07271* (2013.01); *A61B 2017/07278* (2013.01); *A61B 2017/07285* (2013.01); *A61B 2017/2845* (2013.01); *A61B 2017/2912* (2013.01); *A61B 2017/2923* (2013.01)

(58) Field of Classification Search
CPC ........... A61B 2017/07285; A61B 2017/07278; A61B 2017/07271; A61B 2017/2912; A61B 2017/2845; A61B 2017/0046; A61B 2017/0023; A61B 2017/2923
USPC ..... 227/175.1–182.1; 606/73, 139, 142, 143, 606/205, 208
See application file for complete search history.

(56) References Cited

U.S. PATENT DOCUMENTS

| | | | |
|---|---|---|---|
| 5,389,098 A * | 2/1995 | Tsuruta | A61B 17/00234 606/142 |
| 5,417,361 A * | 5/1995 | Williamson, IV | A61B 17/072 227/176.1 |
| 5,529,235 A * | 6/1996 | Boiarski | A61B 17/07207 227/175.1 |
| 5,743,436 A * | 4/1998 | Wilcox | A61C 9/0026 222/137 |
| 8,464,925 B2 * | 6/2013 | Hull | A61B 17/00491 227/179.1 |
| 9,757,130 B2 * | 9/2017 | Shelton, IV | A61B 17/07207 |
| 2002/0198537 A1 | 12/2002 | Smith et al. | |
| 2003/0040759 A1 | 2/2003 | de Guillebon et al. | |
| 2005/0006432 A1 * | 1/2005 | Racenet | A61B 17/07207 227/176.1 |
| 2006/0079913 A1 | 4/2006 | Whitfield et al. | |
| 2006/0097026 A1 | 5/2006 | Shelton et al. | |
| 2008/0210738 A1 | 9/2008 | Shelton et al. | |
| 2009/0090763 A1 * | 4/2009 | Zemlok | A61B 17/07207 227/175.2 |
| 2010/0170931 A1 * | 7/2010 | Viola | A61B 17/128 227/175.1 |
| 2010/0292712 A1 | 11/2010 | Nering et al. | |
| 2011/0174099 A1 * | 7/2011 | Ross | A61B 17/072 74/89.32 |
| 2012/0089131 A1 * | 4/2012 | Zemlok | A61B 17/07207 606/1 |
| 2013/0200131 A1 * | 8/2013 | Racenet | A61B 17/072 227/180.1 |
| 2014/0305992 A1 * | 10/2014 | Kimsey | A61B 17/068 227/176.1 |
| 2015/0209040 A1 * | 7/2015 | Whitman | A61B 17/07207 227/176.1 |
| 2016/0058441 A1 * | 3/2016 | Morgan | A61B 17/0644 606/219 |
| 2016/0058444 A1 * | 3/2016 | Shelton, IV | A61B 17/07207 227/177.1 |
| 2016/0249929 A1 * | 9/2016 | Cappola | A61B 17/068 227/176.1 |
| 2017/0079640 A1 * | 3/2017 | Overmyer | A61B 17/07207 |
| 2017/0224337 A1 * | 8/2017 | Williams | A61B 17/00234 |
| 2017/0281185 A1 * | 10/2017 | Miller | A61B 17/3211 |
| 2017/0281187 A1 * | 10/2017 | Shelton, IV | A61B 17/3211 |
| 2019/0000467 A1 * | 1/2019 | Shelton, IV | A61B 17/07207 |
| 2019/0000477 A1 * | 1/2019 | Shelton, IV | A61B 17/07207 |

* cited by examiner

200

RELOADABLE AND DISPOSABLE MULTIFUNCTIONAL SURGICAL DEVICE

CROSS-REFERENCE TO RELATED APPLICATIONS

The present application is a National Stage Application of PCT International Application No. PCT/FR2014/052926 (filed on Nov. 17, 2014), under 35 U.S.C. § 371, which claims priority to French Patent Application No. 13 61249 (filed on Nov. 18, 2013), which are each hereby incorporated by reference in their respective entireties.

TECHNICAL FIELD

The invention relates to a surgical device, and more particularly a device intended to perform open, endoscopic and/or laparoscopic surgical operations.

BACKGROUND

Numerous surgical techniques are known from the prior art equally well in open surgery and in endoscopic and laparoscopic surgery. Typically, in a surgical procedure, each operative step performed by the surgeon requires the use of a different surgical tool. Indeed, during a procedure, the surgeon may be required to use a plurality of different tools, for example to fit clips or staples of different sizes and shapes, and very regularly in large numbers. Each of these instruments or applicators must be sterilized. Such practices increase the procedure time, the complexity and overall cost associated with these procedures.

A number of prior art documents have proposed providing a surgical device capable of receiving refills of a type of surgical tool, particularly reloadable surgical clip applicators or reloadable staplers, in order to reduce at least partially the overall cost of these procedures.

The document EP 0 760 230 A1 describes a surgical stapler comprising an actuating handle assembly and a disposable loading unit containing a plurality of staples, and an anvil fitted to be adjacent to the staple cartridge and movable being an open position and a closed position.

The document U.S. Pat. No. 6,869,435 B2 describes a surgical instrument suitable for applying surgical fasteners during a surgical procedure. The instrument comprises a functional shaft with functional components, and a removable fastener cartridge equipped with a fastener application mechanism.

Though comprising disposable loading units enabling reuse of the shaft or handle during a surgical operation, the devices of the prior art very often exhibit malfunctions thus invalidating the reusable nature thereof. Indeed, for such reloadable devices, the complementarity of the mechanisms between that comprised in the handle (or shaft) and that comprised in the tool engaging in the handle must be such that, once the tool is engaged in the handle, the device must be operational immediately and in complete safety.

A first aim according to the invention is that of proposing an ergonomic surgical device, that is simple to manufacture and operate, easy to use, and suitable for reducing the time of a surgical procedure.

A further aim according to the invention is that of proposing a suitable device suitable for accomplishing a plurality of different tasks, and notably capable of stapling, applying surgical clips, dissecting, clamping or making an incision.

A further aim according to the invention is that of proposing a surgical device suitable for reducing the overall cost of a surgical procedure.

A final aim according to the invention is that of proposing a surgical device addressing the drawbacks of the devices of the prior art.

SUMMARY

A first aim of the invention relates to a surgical device comprising:
  a handle assembly comprising a casing forming a housing, a stationary handle element, and a movable handle element that can be moved by means of an actuating movement;
  at least one disposable loading unit suitable for being mounted at least partially in a reversible manner inside said casing forming a housing, said disposable loading unit comprising an actuation mechanism;
  said device being characterized in that said casing forming a housing supports:
    a first actuation shaft mounted to make a longitudinal movement inside the housing in response to the movement of the movable handle element;
    a transmission element mounted to actuate a longitudinal movement of a second actuation shaft mounted inside said casing forming a housing in response to the longitudinal movement of the first actuation shaft;
    a main actuation sled and a secondary actuation sled mounted to at least partially receive said at least one disposable loading unit, said actuation sleds being secured respectively to the actuation shafts in order to activate the actuation mechanism of the disposable loading unit in response to the longitudinal movements thereof.

The drive shafts comprise a toothed rack, the transmission element engaging with each of said racks.

Advantageously, the secondary actuation sled is contained in the main actuation sled and is suitable for moving longitudinally by means of a guiding element.

Preferably, the housing further supports a retraction element connected at the proximal end thereof to the first actuation shaft and at the distal end thereof to a fixed support element.

Advantageously, the drive shafts and the actuation sleds each form a single preformed part respectively.

The disposable loading unit preferentially comprises a fastening element engaging at least partially with the proximal part of the body of the disposable loading unit.

The casing forming a housing advantageously comprises an unlocking element, said unlocking element comprising a portion in the form of a projection extending at least partially into the casing in order to engage by locking with the edge of a locking element.

A further aim relates to a kit comprising a surgical device according to the invention, and a plurality of disposable loading units in the form of surgical clip applicators each comprising at least one linear row of surgical clips.

A further aim relates to a kit comprising a device according to the invention and a plurality of disposable loading units preferably selected in the group formed by:
  surgical clip applicators;
  staplers;
  incision tools, notably incision blades.

DRAWINGS

FIG. 1 is a perspective representation of an embodiment of the surgical device according to the invention wherein a disposable loading unit 40 is functionally engaged in the distal part of the casing 10 forming a housing. The arrow "C" illustrates the actuation stroke of the movable handle 13.

FIG. 3b is an exploded view representation of the actuation mechanism in FIG. 3a.

FIG. 4b is an exploded view representation of the disposable loading unit 40 in FIG. 4a.

Figure 5:
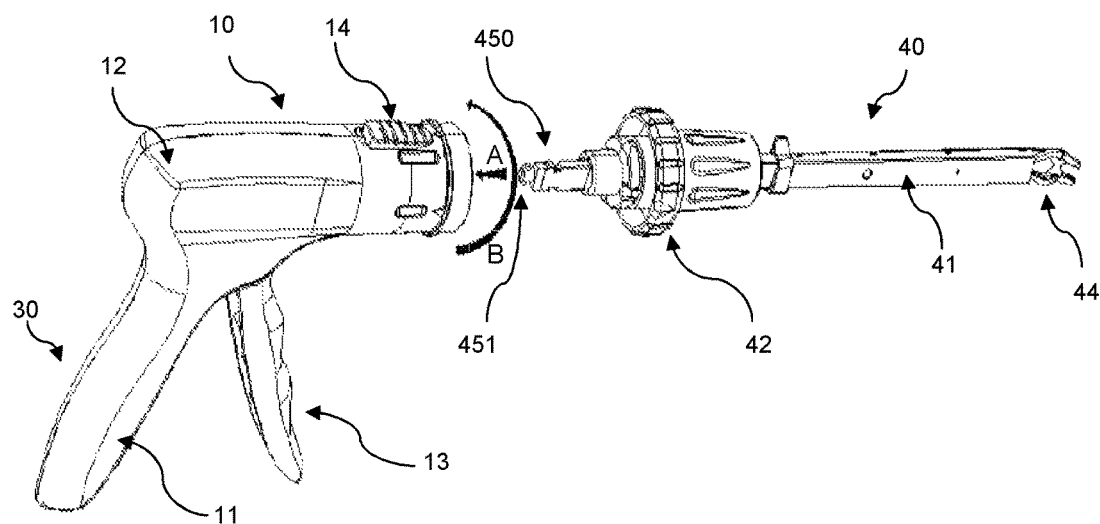

FIG. 5 is a perspective representation of the engagement mechanism of a disposable loading unit 40 on the handle assembly 30 of the surgical device according to the invention. The arrow "A" shows a longitudinal translational movement in the proximal direction of the disposable loading unit 40; the arrow "B" shows a rotational movement of the disposable loading unit 40.

DESCRIPTION

The term "proximal" refers to the end of the device (or apparatus) closest to the operator; the term "distal" refers to the end of the device (or apparatus) furthest from the operator.

Preferred embodiments of the multifunctional surgical device will now be described in detail with reference to the figures. It will be understood that a number of modifications may be made to the embodiments disclosed hereinafter. The description should not be understood to be a restriction of the invention, but merely as exemplifications of preferred embodiments. Obviously, a person skilled in the art can envisage further modifications.

Figure 1:
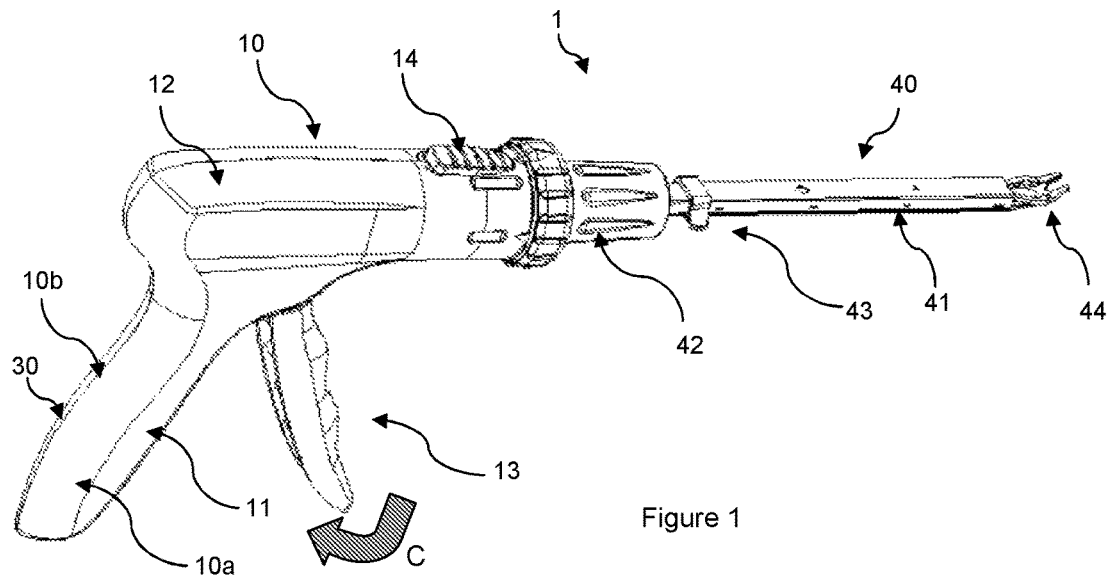
Figure 2A:
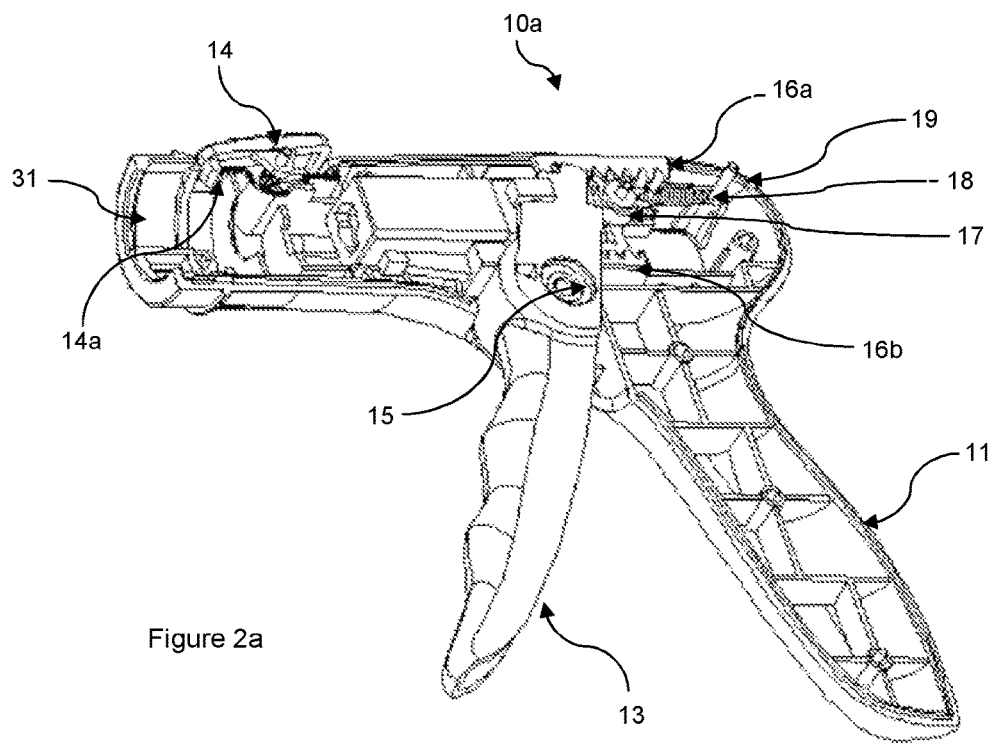
FIG. 2a is a perspective view of the cross-section of the handle assembly 30 of the surgical device.
Figure 2B:
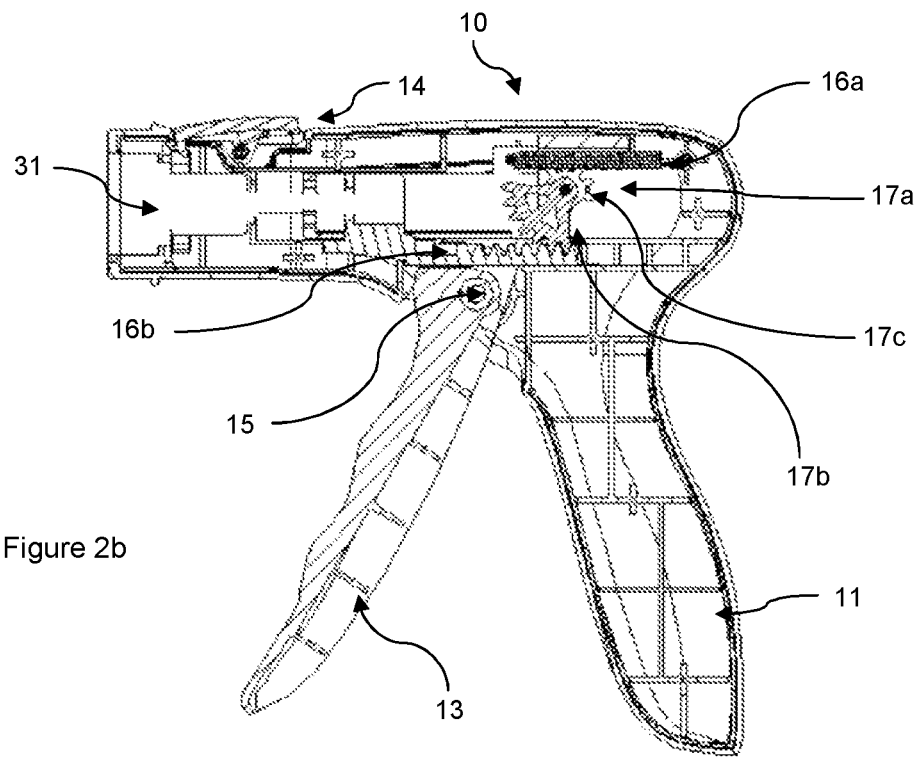
FIG. 2b is a side cross-section view of the handle assembly 30 of the surface device according to the invention.

With reference to FIGS. 1, 2a and 2b, the handle assembly 30 comprises a stationary handle element 11 and a movable handle element 13, and also comprises a casing 10 forming a housing which preferably consists of molded casing half-sections 10a and 10b, which form the stationary handle element 11 and a shaft portion 12 of the handle assembly 30. The handle assembly 30 comprises an opening 31 suitable for receiving a portion of a disposable loading unit 40, as will be described in more detail hereinafter. The movable handle element 13 is supported in a pivoting manner between the casing half-sections 10a and 10b around the pivot 15 (FIG. 2a). A stress element (not shown in the figures), which is preferably a torsion spring, stresses the movable handle 13 away from the stationary handle 11. In the shaft portion 12 are supported two drive shafts 16a, 16b each comprising a toothed rack 160a, 160b. A transmission element 17 (FIG. 2b) engages with each of the two racks 160a, 160b of the drive shafts 16a, 16b and is pivotally mounted about a pivot 17c. More particularly, the transmission element 17 consists of a notched wheel portion 17a suitable for engaging with the rack 160a of the first drive shaft, and a second notched wheel portion 17b suitable for engaging with the rack 160b of the second drive shaft 16b. The rotational axis of both notched wheel portions 17a, 17b is situated at the pivot 17c.

The movable handle 13 can pivot to move the first actuation shaft 16a forward linearly in the distal direction and actuate the transmission element 17 in contact with the toothed rack 160a of said first actuation shaft 16a. The rotation of the transmission element 17 enables the movement of the second actuation shaft 16b linearly in the proximal direction.

The retraction mechanism which comprises a retraction element 18 may be advantageously connected to the proximal end of the first actuation shaft 16a by a traction spring 18. In addition, the traction spring 18 is connected to a fixed support element 19, such that said spring 18 is configured to make a longitudinal translational movement in the distal or proximal direction.

Figure 3A:
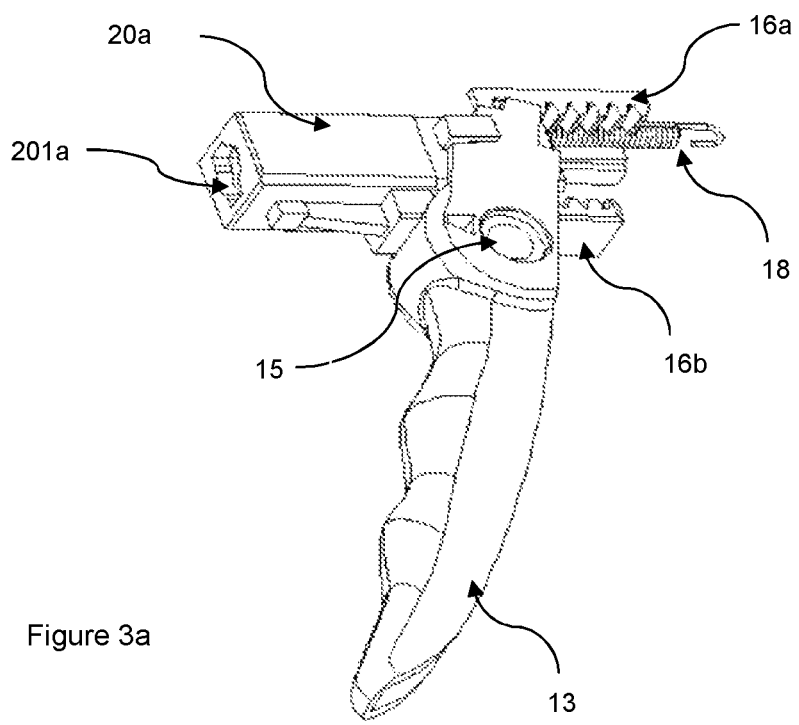
FIG. 3a is a perspective representation of the actuation mechanism supported in the housing 10 of the handle assembly 30.
Figure 3B:
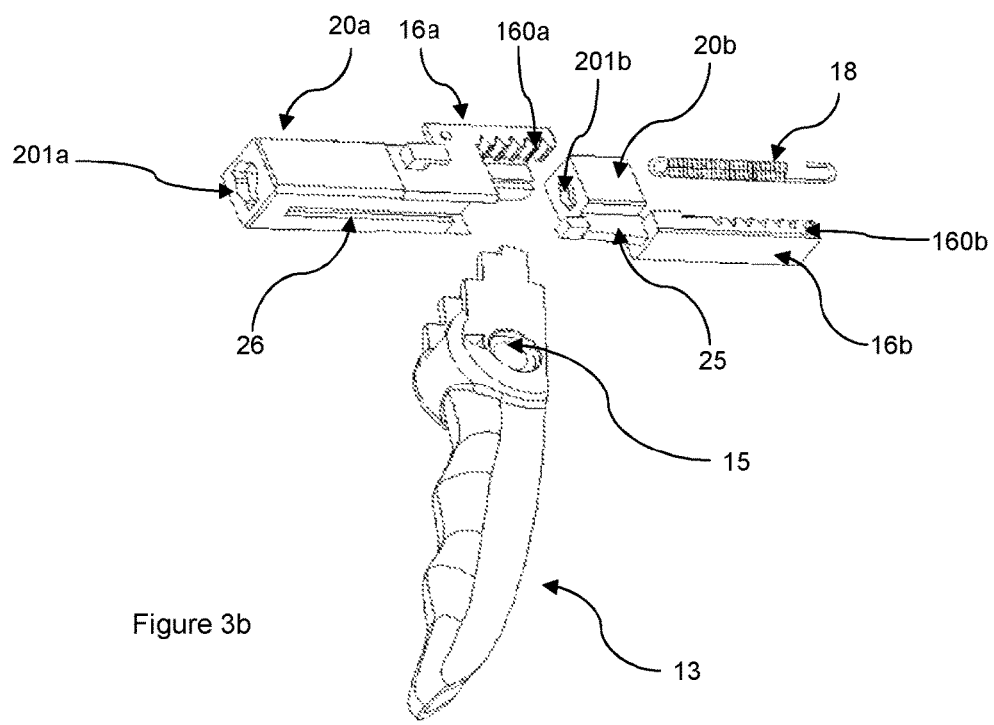

With reference to FIGS. 3a and 3b, the first drive shaft 16a is connected to a main actuation sled 20a comprising at the distal end an opening 201a engaging with the proximal part of the disposable loading unit 40 as described in detail further in the description. The second drive shaft 16b is in turn connected to the secondary actuation sled 20b by means of a guiding element 25. The actuation sled 20b comprises at the distal end thereof an opening 201b engaging with the proximal part of the disposable loading unit 40. In one preferred embodiment, the opening 201b of the secondary actuation sled 20b is smaller in diameter than that of the main actuation sled 20a.

As illustrated more clearly in FIG. 3b, the secondary actuation sled 20b is contained in the actuation sled 20a, and is suitable for moving longitudinally by means of a guide rail 25 suitable for moving in a sliding manner the guiding part 26 on the guide rail 25.

In one preferred embodiment, the drive shafts 16a, 16b and the actuation sleds 20b, 20a each respectively form a single preformed part by molding (FIG. 3b).

With reference to the embodiments in FIGS. 3a and 3b, a fastening mechanism of the disposable loading unit 40 extends into the casing 10 of the handle assembly 30. The fastening mechanism comprises a first actuation sled 20a having a rectangular cross-section which is supported in a sliding manner with the first drive shaft 16a, and a secondary actuation sled 20b having a rectangular cross-section supported in a sliding manner at the second drive shaft 16b. The two distal openings 201a, 201b of the actuation sleds 20a, 20b having a substantially circular shape, and further comprise two additional recesses situated on either side of the opening enabling the passage of the proximal end of the disposable loading unit 40 at the proximal part 45 thereof.

With reference to the embodiments in FIGS. 1, 2 and 3, the casing 10 contains, inter alia, the first drive shaft 16a, the first actuation sled 20a, the second drive shaft 16b and the secondary actuation sled 20b, and the transmission element 17 and the traction element 18; this represents an advantageous embodiment.

Figure 4A:
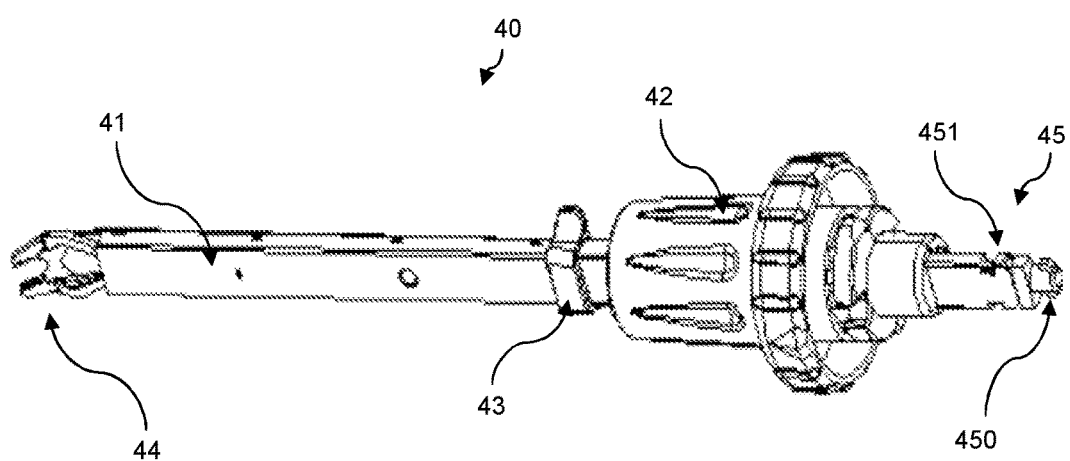
FIG. 4a is a perspective view of a disposable loading unit 40 suitable for being functionally engaged with the handle assembly 30 of the surgical device according to the invention.
Figure 4B:
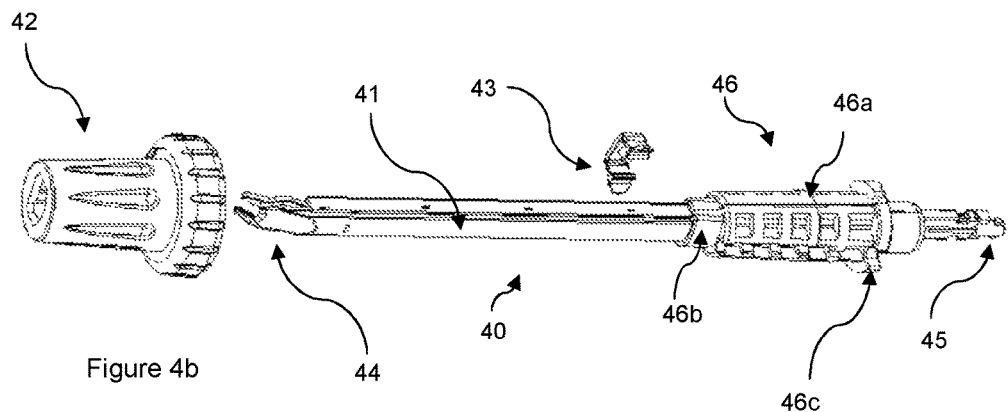

With reference to FIG. 4, the disposable loading unit 40 comprises a proximal portion 45 suitable for engaging releasably with the distal end of the handle assembly 30 (FIG. 1). An actuation mechanism (not shown in the figure) comprised in the body 41 of the disposable loading unit 40 is configured to actuate the tool assembly 44. The proximal portion 45 of the loading unit includes a first pair of hooks 450 and a second pair of hooks 451 suitable for fastening the disposable loading unit 40 on the handle assembly 30, at the distal end of the shaft portion 12 of the casing 10, as will be described in more detail hereinafter. The disposable loading unit 40 further comprises a locking element 46 consisting preferably of molded half-sections 46a and 46b suitable for locking and aligning the mounting assembly comprised in the body of the loading unit. The proximal end of the locking element 46 comprises an edge 46c suitable for engaging with the unlocking element 14 by locking. More particularly, the unlocking element comprises a portion in the form of a projection 14a situated in the recess 10 of the device engaging with the edge 46c of the locking element.

In one advantageous embodiment, the disposable loading unit 40 comprises a fastening element 42 engaging at least partially with the proximal part of the body 41 of the disposable loading unit, and "surrounding" at least partially the locking element 46. The fastening element makes it possible to retain the alignment of the assembly of constituent parts of the body 41, and more particularly the assembly of the actuation mechanism comprised in said body 41. Indeed, in order to function correctly, the assembly of constituent parts of the loading unit 40 must be perfectly aligned with respect to one another, with tolerances of only a few tenths of millimeter, in order to actuate the overall device.

With reference to FIGS. 4 and 5, to use an embodiment of the surgical device according to the invention, a disposable loading unit 40 is first fastened to the distal end of the handle assembly 30. To fasten the disposable loading unit 40 to the handle assembly 30, the proximal portion 45 of the loading unit is inserted into the opening 30a of the handle assembly 30, the first pair of hooks 450 is made slide longitudinally in the distal end of the casing 10 in the direct shown by the arrow "A" in FIG. 5, such that the first pair of hoods 450 is engaged in a first phase through the first actuation sled 20a via to the distal opening 201a, then in a second phase through the second actuation sled 20b via the distal opening 201b. When the first pair of hooks 450 is engaged in the actuation sled 20b, the second pair of hooks 451 is engaged through the actuation sled 20a via the distal opening 201a. Simultaneously, the proximal end of the locking element 46 engages with the unlocking elements 14 by locking.

Once the two pairs of hooks 450, 451 are engaged, the disposable loading unit 40 is made rotate in the direction shown by the arrow "B" in FIG. 5 to engage the pairs of hooks 450, 451 with the inner shoulders of the distal ends of the actuation sleds 20a, 20b. It should be noted that, when the disposable loading unit is made rotate, an audible click sound is produced indicating that the disposable loading unit 40 is fastened correctly to the housing 10.

When the disposable loading unit 40 is fastened to the casing 10, the tool 45 can be used and positioned to dispense a plurality of clips. For this purpose, the movable handle 13 is moved in the direction shown by the arrow "C" in FIG. 1 against the stress of the torsion spring to make the first actuation shaft 16a move forward linearly in the distal direction and to move the second actuation shaft 16b forward linearly in the proximal direction by means of the transmission element 17.

The movement of the actuation shafts 16a, 16b induces the movement of the respective actuation sleds 20a, 20b thereof. The disposable loading unit 40 being fastened to the handle 30, the movement of the actuation sled 20b induces therewith the movement in the proximal direction of the first pair of hooks 450 which is rigidly connected to a first plate (not shown in the figures). The first plate thus moves longitudinally in the proximal direction until it engages with a clip "n−1" stored in the body 43 of the movable loading unit 40. Simultaneously, the movement of the actuation sled 20a induces therewith the movement in the distal direction of the second pair of hooks 451 which is in turn rigidly connected to a second plate (not shown in the figures) suitable for moving a clip "n" in the distal direction, i.e. toward the tool assembly 44. Furthermore, associated with the movement of the pair of hooks 451, a third plate (not shown in the figures) is actuated in the distal direction toward the tool assembly 44 enabling the actuation thereof, notably making it possible in the case of a clip applicator to close the jaws of the tool assembly around the clip "n".

Advantageously, the disposable loading unit 40 further comprises a securing element 43 situated at least partially on the body 41 of the loading unit to retain the alignment of the clips comprised in the body 41 before the use of the device, notably when the device is transported or stored. During the use of the device 1, the securing element 43 must be removed to activate the various clip dispensing mechanisms.

With reference once again to FIG. 1, the invalidated or locked disposable loading unit 40 can be removed from the casing 10 by applying a pressure to the unlocking element 14, then by rotating the disposable loading unit 40 in the opposite direction of the direct shown by the arrow "B" in FIG. 5 to disengage the pairs of hooks 450, 451 on the inner shoulders of the actuation sleds 20a, 20b. After rotation, the disposable loading unit 40 can be made slide in the opposite direction to that shown by the arrow "A" in order to detach the casing 10 from the disposable loading unit 40. Subsequently, additional disposable loading units can be fastened to the distal end of the casing 10, as described above, to perform the same operation, i.e. dispensing clips, or to perform further tasks, for example stapling tissue, an incision, a section operation.

The device according to the invention thus comprises a simplified mechanism reducing tooling and assembly requirements considerably, while offering very good operational reliability, at least cost. In order to function correctly, the device according to the invention requires small general tolerances. By way of illustration, the general tolerances relating to the sizing of the clips are as follows: ±0.30 mm on all the plane faces of the clip, ±0.4 mm for the height, ±0.40 mm width of the clip between the jaws of a tool assembly.

The disposable loading unit 40 may comprise at least one linear row of at most thirty clips, preferably at most twenty clips. These clips are used to ligate blood vessels, notably arteries, or before sectioning same or assembling organic or synthetic tissue. The clips may be absorbable or non-absorbable, in the latter case, the clips are preferably made of titanium and substantially U-shaped. Furthermore, the length of the linear row of surgical clips or staples may be modified to meet the needs of a specific surgical procedure.

Obviously, a number of modifications may be made to the embodiments described above. For example, the device according to the invention does not necessarily apply only surgical clips (or surgical fasteners) but may also apply staples, for example for the ablation of all or part of an organ and/or to make it possible to carry out anastomosis. As such, the device may be used with disposable loading units designed to apply linear rows of staples and may be used to activate disposable loading units containing individual staples.

The device according to the invention may also support in the housing thereof a disposable loading unit wherein the distal end part supports a blade configured to make incisions, for example an incision in stapled body tissue.

LIST OF REFERENCE SYMBOLS

| | |
|---|---|
| 1 | Device |
| 10 | Casing |

-continued

| | |
|---|---|
| 11 | Stationary handle element |
| 12 | Shaft portion |
| 13 | Movable handle element |
| 14 | Unlocking element |
| 15 | Pivot |
| 16a | First actuation shaft |
| 16b | Second actuation shaft |
| 17 | Transmission element |
| 18 | Traction element |
| 19 | Support element |
| 20a | Main actuation sled |
| 20b | Secondary actuation sled |
| 25 | Guide rail |
| 26 | Guiding part |
| 30 | Handle assembly |
| 31 | Opening |
| 40 | Disposable loading unit |
| 41 | Body |
| 42 | Fastening element |
| 43 | Securing element |
| 44 | Tool assembly |
| 45 | Proximal portion |
| 46 (46a, 46b) | Locking element |
| 46c | Peripheral edge of locking element |
| 160a, 160b | Toothed racks |
| 201a, 201b | Distal openings |
| 450 | Lower dental canal |
| 451 | Horizontal partition |

What is claimed is:

1. A kit, comprising:
a surgical device including:
  a handle assembly including a casing forming a housing, a stationary handle element, and a movable handle element that can be moved by way of an actuating movement;
  a disposable loading unit to be mounted inside said casing, the disposable loading unit including at least one linear row of surgical clips,
wherein the casing is to contain therein:
  a first actuation shaft mounted for longitudinal movement inside the housing in response to movement of the movable handle element;
  a second actuation shaft;
  a transmission element to actuate a longitudinal movement of the second actuation shaft in response to the longitudinal movement of the first actuation shaft; and
  a main actuation sled and a secondary actuation sled mounted to at least partially receive the disposable loading unit, the main actuation sled and the secondary actuation sled being secured respectively to the first actuation shaft and the second actuation shaft to activate an actuation mechanism of the disposable loading unit in response to the longitudinal movement of the first actuation shaft and the second actuation shaft,
wherein the first actuation shaft and the second actuation shaft respectively comprise a toothed rack to be engaged by the transmission element.

2. The kit of claim 1, wherein the secondary actuation sled is contained in the main actuation sled, and is movable longitudinally by way of a guiding element.

3. The kit of claim 1, wherein the housing further supports a retraction element connected at a proximal end thereof to the first actuation shaft, and at the distal end thereof to a fixed support element.

4. The kit of claim 1, wherein the first actuation shaft, the second actuation shaft, the main actuation sled, and the secondary actuation sled each respectively form a single preformed part.

5. The kit of claim 1, wherein the first actuation shaft, the second actuation shaft, the main actuation sled, and the secondary actuation sled each respectively form a single molded preformed part.

6. The kit of claim 1, wherein the disposable loading unit comprises a fastening element to engage at least partially with a proximal part of a body of the disposable loading unit.

7. The kit of claim 1, wherein the casing comprises an unlocking element, the unlocking element including a projection extending at least partially into the casing in order to engage by locking with an edge of a locking element of the disposable loading unit.

8. A surgical device, comprising:
a handle assembly including a housing defining a stationary handle element and a movable handle element;
a first actuation shaft arranged in the housing for movement in response to movement of the movable handle element;
a second actuation shaft arranged in the housing for movement therein;
a transmission element to actuate the movement of the second actuation shaft in response to the movement of the first actuation shaft;
a fastening mechanism to include a main actuation sled to be supported in a sliding manner with the first actuation shaft, and a secondary actuation sled to be supported in a sliding manner at the second actuation shaft; and
a disposable loading unit to releasably engage said housing assembly, the disposable loading unit having a body to store at least one surgical clip, and an actuation mechanism to be activated by the main actuation sled in response to the longitudinal movement of the first actuation shaft and the second actuation shaft,
wherein the first actuation shaft and the second actuation shaft respectively comprise a toothed rack to be engaged by the transmission element.

9. The surgical device of claim 8, wherein the secondary actuation sled is contained in the main actuation sled, and is movable longitudinally by way of a guiding element.

10. The surgical device of claim 8, further comprising a retraction element arranged in the housing to be connected at a proximal end thereof to the first actuation shaft, and at the distal end thereof to a fixed support element.

11. The surgical device of claim 8, wherein the first actuation shaft, the second actuation shaft, the main actuation sled, and the secondary actuation sled respectively form a single preformed part.

12. The surgical device of claim 8, wherein the first actuation shaft, the second actuation shaft, the main actuation sled, and the secondary actuation sled each respectively form a single molded preformed part.

13. The surgical device of claim 8, wherein the disposable loading unit comprises a fastening element to engage at least partially with a proximal part of the body of the disposable loading unit.

14. The surgical device of claim 8, further comprising an unlocking element arranged in the housing, the unlocking element including a projection extending at least partially into the casing to engage by locking with an edge of a locking element of the disposable loading unit.

15. A surgical device, comprising:
a handle assembly including a stationary handle element and a movable handle element;

a first actuation shaft configured for movement in response to movement of the movable handle element;

a second actuation shaft configured movement in response to the movement of the first actuation shaft;

a fastening mechanism to include a main actuation sled to be operatively connected to the first actuation shaft, and a secondary actuation sled to be operatively connected to the second actuation shaft; and a disposable loading unit having a body to store at least one surgical clip, and an actuation mechanism to be activated by the main actuation sled in response to the longitudinal movement of the first actuation shaft and the second actuation shaft, wherein the first actuation shaft and the second actuation shaft respectively comprise a toothed rack to be engaged by the transmission element.

* * * * *